(12) United States Patent
Bloom

(10) Patent No.: US 9,102,600 B2
(45) Date of Patent: Aug. 11, 2015

(54) DMSO PURIFICATION

(71) Applicant: DMSO SOLUTIONS, LLC, Bogalusa, LA (US)

(72) Inventor: Claude Bloom, Bogalusa, LA (US)

(73) Assignee: DMSO SOLUTIONS, LLC, Bogalusa, LA (US)

( * ) Notice: Subject to any disclaimer, the term of this patent is extended or adjusted under 35 U.S.C. 154(b) by 49 days.

(21) Appl. No.: 14/069,621

(22) Filed: Nov. 1, 2013

(65) Prior Publication Data

US 2015/0126780 A1     May 7, 2015

(51) Int. Cl.
| | |
|---|---|
| *C07C 317/02* | (2006.01) |
| *C07C 315/06* | (2006.01) |
| *B01D 9/00* | (2006.01) |

(52) U.S. Cl.
CPC .............. *C07C 315/06* (2013.01); *B01D 9/00* (2013.01)

(58) Field of Classification Search
USPC .................................................. 568/18, 27
See application file for complete search history.

(56) References Cited

U.S. PATENT DOCUMENTS

| | | | |
|---|---|---|---|
| 3,045,051 A | | 7/1962 | Coma et al. |
| 3,358,037 A | | 12/1967 | Allegretti et al. |
| 3,419,619 A | * | 12/1968 | Soder et al. ............ 568/27 |
| 3,708,542 A | | 1/1973 | Douchet et al. |
| 5,090,965 A | | 2/1992 | Kehm et al. |
| 6,414,194 B1 | * | 7/2002 | Bloom et al. ............ 568/27 |
| 2014/0161663 A1 | * | 6/2014 | Farren et al. ............ 422/24 |

OTHER PUBLICATIONS

Dimethyl Sulfoxide (DMSO) Physical Properties, Gaylord Chemical Corporation Bulletin #101, Dec. 1998.
Philippe et al.,"Etude critique des dierents modes de purification du dimethylsufoxyde", Bull. Soc. Chem. France No. 11, p. 4713-4716, 1968 Plus English translation.
Information Disclosure Statement Excerpted from the Prosecution History of U.S. Appl. No. 09/557,237 which ultimately issued as U.S. Pat. No. 6,414,194, dated Dec. 22, 2000.

* cited by examiner

*Primary Examiner* — Sudhakar Katakam
*Assistant Examiner* — Pancham Bakshi
(74) *Attorney, Agent, or Firm* — John B. Edel; Edel Patents LLC

(57) ABSTRACT

Methods and apparatus for purifying DMSO are disclosed including a method of purifying DMSO involving providing a first DMSO composition having impurities; freezing a portion of the first DMSO composition on a first surface to form a second DMSO composition having higher DMSO purity than the first DMSO composition such that a third DMSO composition remains from the unfrozen portion of the first DMSO composition; separating the second DMSO composition from the third DMSO composition; and melting a portion of the second DMSO composition. The freezing of the portion of the first DMSO composition, the separating of the second DMSO composition from the third DMSO composition, and the melting of the portion of the second DMSO composition may happen simultaneously. DMSO purification apparatus employing such methods and other methods are also taught.

18 Claims, 2 Drawing Sheets

DMSO PURIFICATION

The DMSO purification processes described herein may be used in the preparation of pharmaceutical grade DMSO compositions. Certain DMSO purification processes disclosed herein provide DMSO purification at high levels of efficiency.

DMSO purification apparatus described herein may, for example, comprise a first surface; a second surface; a DMSO supply; and a purified DMSO discharge; wherein the first surface is a first heat conducting surface; wherein the second surface is a second heat conducting surface; wherein the first surface is arranged and configured to freeze DMSO; and wherein the second surface is arranged and configured to melt DMSO at the same time the first surface freezes DMSO. In certain embodiments the first surface is a part of a chilled drum. The DMSO purification apparatus may further comprise a vessel containing a volume of DMSO. The volume of DMSO may be adjacent to the first surface. In certain embodiments the volume of DMSO is mixed. In certain related embodiments, the chilled drum is arranged and configured to rotate through a volume of liquid DMSO thereby freezing a portion of the volume of liquid DMSO to the chilled drum. Certain further related embodiments may have a mechanical separator arranged and configured to direct a quantity of solid purified DMSO to the second heat conducting surface.

Methods of purifying DMSO described herein may, for example, comprise providing a first DMSO composition having impurities; freezing a portion of the first DMSO composition on a first surface to form a second DMSO composition having higher DMSO purity than the first DMSO composition whereby a third DMSO composition remains from an unfrozen portion of the first DMSO composition; separating the second DMSO composition from the third DMSO composition; melting a portion of the second DMSO composition; wherein the freezing of the portion of the first DMSO composition, the separating of the second DMSO composition from the third DMSO composition, and the melting of the portion of the second DMSO composition happen simultaneously. In certain embodiments, the freezing of the portion of the first DMSO composition may be carried out continuously for a period of time greater than 10 hours. In certain related embodiments, the freezing of the portion of the first DMSO composition may be carried out continuously for a period of time greater than 20 hours. In certain further related embodiments, the freezing of the portion of the first DMSO composition on the first surface has an efficient freezing duration greater than 50 minutes. In certain further related embodiments, the freezing of the portion of the first DMSO composition on the first surface may be done such that a maintained DMSO ice thickness is less than 0.2 inches. In certain further related embodiments, the freezing of the portion of the first DMSO composition on the first surface may be done such that a maintained DMSO ice thickness is less than 0.4 inches. In certain further related embodiments, the freezing of the portion of the first DMSO composition on the first surface may be done such that the percentage of a batch of crude DMSO frozen in a single continuous freezing operation is greater than 25%. In certain further related embodiments, the productivity per square foot of DMSO submerged heat transfer surface during a continuous four hour freezing operation is greater than 15 $lb_m/ft^2$. In certain further related embodiments, the freezing of the portion of the first DMSO composition on the first surface to form the second DMSO composition is done in a single continuous freezing operation. In certain further related embodiments, the percentage of DMSO converted to purified DMSO from a batch of crude DMSO is greater than 50%. In certain further related embodiments, water may be added to the first DMSO composition prior to the step of freezing the portion of the first DMSO composition. In certain further related embodiments, ultraviolet germicidal irradiation may be applied to the second DMSO composition. In certain further related embodiments, the first surface may be part of a rotating drum. In certain further related embodiments, the first surface may be part of an apparatus that is internally cooled. In certain further related embodiments, the first DMSO composition may be mixed.

DETAILED DESCRIPTION

Example 1

Figure 1:
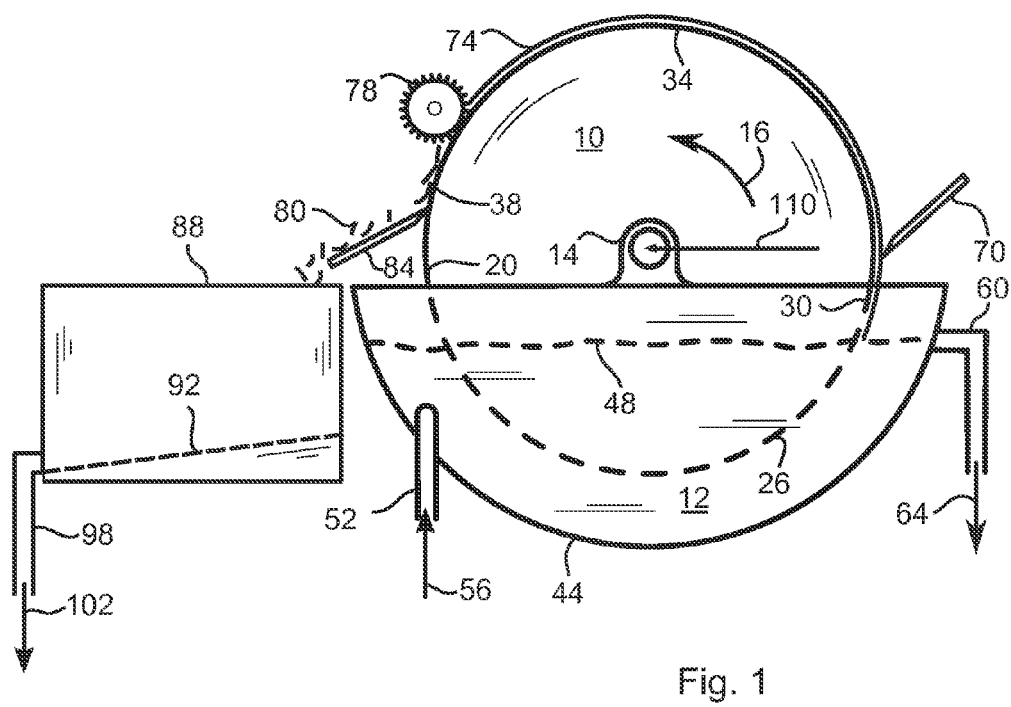
FIG. 1 depicts a freezing drum and associated equipment.

Referring now to FIG. 1 of the drawings, Freezing drum 10 is used to crystallize and/or freeze DMSO. Freezing drum 10 is supported along its axis by Drum bearings 14 suspended such that Freezing drum 10 is located partially within Drum pan 44 and such that Freezing drum 10 is partially submerged in DMSO pool 12. DMSO pool 12 may be mixed solely by movement of Freezing drum 10 and the movement of other fluids from the process or by the use of an agitator (not shown). Freezing drum 10 rotates in Drum rotation direction 16 such that Clean drum section 20 rotates into DMSO pool 12 such that the surface of Freezing drum 10 at Drum freezing section 26 accumulates a layer of DMSO ice. As Drum freezing section 26 rotates out of DMSO pool 12 a layer of DMSO ice with a small layer of liquid DMSO emerges from DMSO pool 12 at Wet frozen drum section 30. Liquid DMSO wiper blade 70 then removes the remaining liquid DSMO from Freezing drum 10 with the remaining liquid DMSO draining over Wet frozen drum section 30 back into DMSO pool 12. Beyond Liquid DMSO wiper blade 70 Dry DSMO ice sheet 74 sits atop Dry frozen drum section 34. Dry DSMO ice sheet 74 is pure or nearly pure DMSO ice. Pin crusher 78 then breaks up the DMSO ice such that Crushed DMSO ice 80 either falls past Broken ice drum section 38 or travels along Broken ice drum section 38 such that Crushed DMSO ice 80 departs from Freezing drum 10 at DMSO ice scraper 84. The Crushed DMSO ice 80 then travels by gravity to Melting vessel 88 where it melts on Melting plate 92. Melted purified DSMO then flows by gravity from Melting vessel 88 down Purified DSMO discharge 102 through Purified DSMO discharge line 98. The temperature of Freezing drum 10 is maintained below the freezing point of the DMSO in DMSO pool 12 by the addition of coolant to Freezing drum 10 through Drum coolant inlet 110. The coolant may be propylene glycol, DMSO and water, or other compositions suitable for the operating temperature of the equipment.

DMSO pool 12 may be continuously fed DMSO by Drum pan DMSO supply 56 through Drum pan DMSO supply line 52. The Liquid level 48 of DMSO pool 12 is maintained by gravity overflow of DMSO pool 12 through Drum pan DMSO overflow 64 which travels through Drum pan DMSO overflow line 60.

Figure 2:
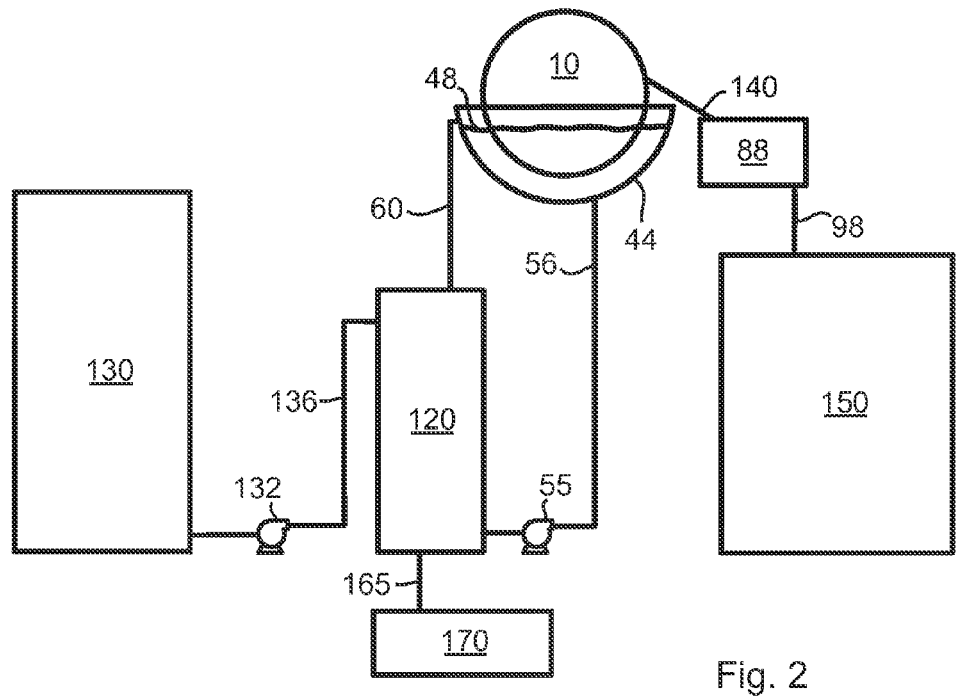
FIG. 2 shows a process for purifying DMSO including a freezing drum.

FIG. 2 of the drawings shows a process in which the drum freezing equipment of FIG. 1 may operate. DSMO is supplied from Un-purified DSMO storage tank 130 through Un-purified DSMO supply pump 132 and Un-purified DSMO supply line 136 to DMSO drum supply tank 120. DMSO drum supply tank 120 may begin empty and may be charged with raw DSMO from Un-purified DSMO storage tank 130. Around the time that DMSO drum supply tank 120 is fully charged DMSO drum supply pump 55 fills Drum pan 44 to Liquid level 48 through Drum pan DMSO supply line 56. A motor (not shown) drives Freezing drum 10 such that the freezing process described above operates to freeze and purify DMSO for melting in Melting vessel 88. Drum pan 44 overflows by Drum pan DMSO overflow line 60 maintaining a constant Liquid level 48 in Drum pan 44. Crushed DMSO ice 80 travels along Drum ice discharge path 140 to Melting vessel 88 where it is melted and ultimately travels down Purified DSMO discharge line 98 to Purified melted DMSO storage tank 150 for storage and later use. As Freezing drum 10 operates in this manner to produce purified DMSO in Purified melted DMSO storage tank 150, the liquid level in DMSO drum supply tank 120 decreases and at the same time the concentration of impurities in the DMSO within DMSO drum supply tank 120 increases. Depending on the purity requirements for the DMSO being produced and/or the concentration of impurities within DMSO drum supply tank 120 a decision may be made to dispose of or recycle the contents of DMSO drum supply tank 120 and Drum pan 44. At that point, Freezing drum 10 is stopped, Drum pan 44 is drained back to DMSO drum supply tank 120 with the assistance of an additional drain line (not shown), and DMSO drum supply tank 120 is drained to Spent DMSO discharge tank 170 by way of Spent DMSO discharge line 165. With DMSO drum supply tank 120 substantially empty an additional charge of DMSO is taken from Un-purified DSMO storage tank 130 such that the purification process repeats.

As used herein, the terms "frozen" and "ice" generally refer to the solid form of DMSO regardless of whether that DMSO is in crystalline form. Accordingly, the terms "freeze" and "freezing" generally refer to the process of making frozen DMSO.

Optionally, the process depicted in FIG. 2 could be modified to include one or more additional drums comparable to Freezing drum 10 such that the DMSO freezing and melting process would reoccur a number of additional times corresponding to the number of additional drums. In such a configuration, the purity of the DMSO would sequentially increase with each freezing. The number of drums in such a configuration could be two, three, four, or more. As a further related option, the purification process could be configured with a single drum and piped such that the purified DMSO product could be returned to DMSO drum supply tank 120 for reprocessing in a similar manner allowing one or more additional purifications of the DMSO. Such a process could provide DMSO at purity levels not obtainable through a single freeze and melt processing.

Example 2

A series of related embodiments may be characterized by one or more of the features described in Examples 2A-2AA. Among the embodiments that may have those characteristics is the embodiment described generally as Example 1. However, a wide range of other embodiments may also share the described features. As described herein, a batch of crude DMSO is a quantity of DMSO that is substantial with respect to the DMSO submerged heat exchange surface area used to freeze the batch of crude DMSO. Specifically, as that term is used herein a "batch" of crude or unpurified DMSO in the context of purification processes described herein is a quantity of DMSO that is at least 30 $lb_m$ of DMSO for every square foot of DMSO submerged heat exchange surface area used to freeze the batch of crude DMSO in the purification process.

The surface on which the DMSO is frozen may operate for several hours of continuous freezing and the examples presented below in Table 1 characterize the duration of that continuous freezing in hours as the "continuous freeze time."

The configuration of the heat exchange surface for freezing such as the configuration described in Example 1 allow for the continued cleaning of the freezing heat transfer surface and ultimately provide high production rates for longer periods of time. The time in minutes of continuously sustained DMSO freezing above 0.09 $lb_m/(min.*ft^2)$ of DMSO submerged heat transfer surface is presented below in Table 1 as the "efficient freezing duration."

Further, embodiments described herein may operate with relatively thin DMSO ice on the heat exchange surfaces allowing better heat transfer and that thin DMSO ice is maintained for freezing periods exceeding one hour. The thickness of DMSO ice maintained during a continuous freezing operation of at least one hour is measured in inches and the examples presented below in Table 1 characterize that thickness as the "maintained DMSO ice thickness."

TABLE 1

|  | Continuous freeze time | Efficient freezing duration | Maintained DMSO ice thickness |
|---|---|---|---|
| Example 2A | >10 | >50 | <0.2 |
| Example 2B | >20 | >50 | <0.2 |
| Example 2C | >30 | >50 | <0.2 |
| Example 2D | >10 | >200 | <0.2 |
| Example 2E | >20 | >200 | <0.2 |
| Example 2F | >30 | >200 | <0.2 |
| Example 2G | >10 | >600 | <0.2 |
| Example 2H | >20 | >600 | <0.2 |
| Example 2I | >30 | >600 | <0.2 |
| Example 2J | >10 | >50 | <0.4 |
| Example 2K | >20 | >50 | <0.4 |
| Example 2L | >30 | >50 | <0.4 |
| Example 2M | >10 | >200 | <0.4 |
| Example 2N | >20 | >200 | <0.4 |
| Example 2O | >30 | >200 | <0.4 |
| Example 2P | >10 | >600 | <0.4 |
| Example 2Q | >20 | >600 | <0.4 |
| Example 2R | >30 | >600 | <0.4 |
| Example 2S | >10 | >50 | <0.6 |
| Example 2T | >20 | >50 | <0.6 |
| Example 2U | >30 | >50 | <0.6 |
| Example 2V | >10 | >200 | <0.6 |
| Example 2W | >20 | >200 | <0.6 |
| Example 2X | >30 | >200 | <0.6 |
| Example 2Y | >10 | >600 | <0.6 |
| Example 2Z | >20 | >600 | <0.6 |
| Example 2AA | >30 | >600 | <0.6 |

Example 3

A series of related embodiments may be characterized by one or more of the features described in Examples 3A-3R. Among the embodiments that may have those characteristics is the embodiment described generally as Example 1. However, a wide range of other embodiments may also share the described features.

Embodiments described herein may convert a large percentage of a batch of crude DMSO into frozen DMSO in a single continuous freezing operation. The percentage of a batch of crude DMSO frozen in a single continuous freezing operation is presented below in Table 2 as the "single freeze percentage."

The configuration of the heat exchange surface also allows for a large quantity of DMSO to be frozen during a continuous freezing operation. The productivity per square foot of DMSO submerged heat transfer surface during a continuous four hour freezing operation measured in $lb_m/ft^2$ is presented below in Table 2 as the "4 hr. productivity."

The continuous operation of the DMSO freezing equipment allows the freezing of a large volume of DMSO in a single continuous freezing operation. The number of separate continuous freezing operations applied to a batch of crude DMSO is presented below in Table 2 as the "freezes per batch."

Similarly, the percentage of DMSO converted to purified DMSO from a single batch may be relatively large compared to other processes. The percentage of DMSO converted to purified DMSO from a batch of crude DMSO is presented below in Table 2 which characterizes that percentage as the "batch conversion percentage."

TABLE 2

|  | Single Freeze Percentage | 4 hr. productivity | Freezes per batch | Batch conversion percentage |
| --- | --- | --- | --- | --- |
| Example 3A | >25 | >15 | 1 | >50 |
| Example 3B | >25 | >15 | ≤3 | >50 |
| Example 3C | >25 | >20 | 1 | >50 |
| Example 3D | >25 | >20 | ≤3 | >50 |
| Example 3E | >25 | >30 | 1 | >50 |
| Example 3F | >25 | >30 | ≤3 | >50 |
| Example 3G | >50 | >15 | 1 | >50 |
| Example 3H | >50 | >15 | ≤3 | >50 |
| Example 3I | >50 | >20 | 1 | >50 |
| Example 3J | >50 | >20 | ≤3 | >50 |
| Example 3K | >50 | >30 | 1 | >50 |
| Example 3L | >50 | >30 | ≤3 | >50 |
| Example 3M | >70 | >15 | 1 | >50 |
| Example 3N | >70 | >15 | ≤3 | >50 |
| Example 3O | >70 | >20 | 1 | >50 |
| Example 3P | >70 | >20 | ≤3 | >50 |
| Example 3Q | >70 | >30 | 1 | >50 |
| Example 3R | >70 | >30 | ≤3 | >50 |

The 27 individual examples of Example 2 may be combined with any of the 18 individual examples of Example 3 to describe equipment and methods consistent with the present disclosure. For example, the combination of Example 2A and 3A represents a system having a continuous freeze time greater than 10 hours, an efficient freezing duration greater than 50 minutes, a maximum DMSO ice thickness of 0.2 inches, a single freeze percentage greater than 25%, a 4 hr. productivity greater than 15 $lb_m/ft^2$, a freezes per batch of 1, and a batch conversion percentage greater than 50%.

Example 4

Figure 3:
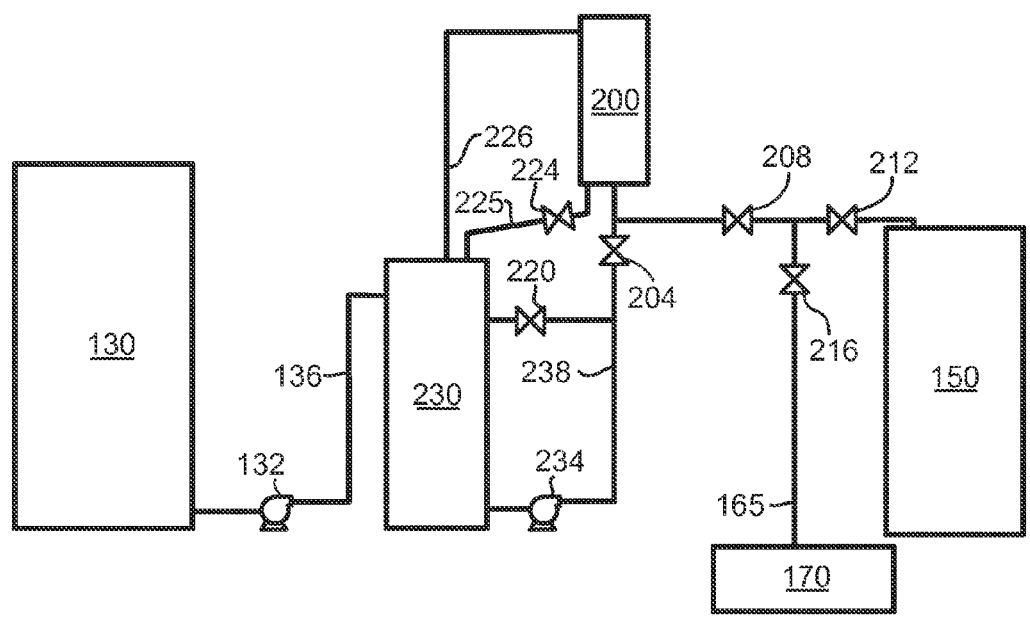
FIG. 3 shows another process for purifying DMSO.

Referring now to FIG. 3 of the drawings, Un-purified DSMO storage tank 130 stores unpurified DMSO. At the beginning of a batch process cycle a charge of DMSO is transported from Un-purified DSMO storage tank 130 to Melt crystallization storage tank 230 by way of Un-purified DSMO supply pump 132 and Un-purified DSMO supply line 136. That charge is then purified in a cyclic process that involves filling Melt crystallization tank 200 through DMSO purification supply pump 234, DMSO purification supply line 238, and Melt crystallization supply valve 204. Melt crystallization recycle valve 220 and Melt crystallization discharge valve 208 are held closed during the initial filling of Melt crystallization tank 200. Although the configuration of Melt crystallization tank 200 may vary, it is designed to freeze a substantial portion of the DMSO it contains then drain the unfrozen mother liquor back to Melt crystallization storage tank 230 for example through Mother liquor primary drain line 225 and Mother liquor primary drain line valve 224. After the mother liquor is completely drained the system of valves is configured such that Melt crystallization tank 200 drains to Purified melted DMSO storage tank 150 and the frozen DSMO crystal is melted. For example, during the melting of the purified DMSO, Mother liquor primary drain line valve 224, Spent DMSO discharge valve 216, and Melt crystallization supply valve 204 may be closed and Melt crystallization discharge valve 208 and Purified DMSO discharge valve 212 may be open. Melt crystallization tank 200 is then filled again, partially frozen, and the steps are repeated such that the mother liquor from Melt crystallization tank 200 is repeatedly drained back to Melt crystallization storage tank 230 and the purified DMSO is repeatedly drained to Purified melted DMSO storage tank 150. After a significant number of cycles the mother liquor remaining in Melt crystallization storage tank 230 will have a concentration of impurities which is either unacceptable for further purification or not economically justified and the remaining mother liquor is pumped to Spent DMSO discharge tank 170 by way of Spent DMSO discharge line 165 through Spent DMSO discharge valve 216. After the preceding batch has been cleared from Melt crystallization tank 200 and Melt crystallization storage tank 230 a batch of DMSO is supplied to Melt crystallization storage tank 230 from Un-purified DSMO storage tank 130 and that batch is processed in a similar manner.

In certain embodiments, a nitrogen blanket may be used in various process equipment to minimize moisture absorption from the air into the DMSO. Further, pressurized nitrogen may be used in certain embodiments to move liquid DMSO or other liquids through the process in lieu of pumping those liquids.

Mixing may be maintained in Melt crystallization tank 200 either through the use of an agitator (not shown) or through the circulation of DMSO from Melt crystallization storage tank 230 by DMSO purification supply pump 234.

Example 5

Referring to FIG. 3 of the drawings, Melt crystallization tank 200 may be configured such that when frozen mother liquor on the heat exchange surfaces of Melt crystallization tank 200 is approximately 1 inch thick the quantity unfrozen mother liquor in Melt crystallization tank 200 is roughly equivalent to the quantity of unfrozen mother liquor and Melt crystallization tank 200. As an example, Melt crystallization storage tank 230 may be roughly 10 times the volume of Melt crystallization tank 200. In such an embodiment, Melt crystallization tank 200 may be charged full of DMSO mother liquor, frozen to a DMSO ice thickness of 1 inch and further treated as described above to deliver purified DMSO to Purified melted DMSO storage tank 150. The charging of Melt crystallization tank 200 with DMSO mother liquor, freezing, separating, thawing, and draining would be repeated until on the 19$^{th}$ and final charge of Melt crystallization tank 200 the DMSO mother liquor not frozen in the final freeze cycle would be disposed of in Spent DMSO discharge tank 170. In most cases, the discharged mother liquor would contain the majority of contaminants from the original contents of Melt crystallization storage tank 230.

Example 6

In one embodiment, crude DMSO is mixed with water prior to the freezing of the DMSO. The DMSO is subjected to a freezing process such as the freezing processes described in the preceding examples. Due to the additional water present in the DMSO, the resulting mother liquor left after freezing will have an elevated water concentration. Based on an evaluation of the water concentration, the temperature at which the mother liquor is freezing, the percentage of DMSO that has been purified from a particular batch, or other relevant variables the process may temporarily be stopped for a freeze off operation. The process temporarily being stopped may for example be the process of Example 1 or the process of Example 4. The freeze off operation may for example include lowering the temperature of the mother liquor until substantially all of the DMSO in the mother liquor is frozen leaving a quantity of unfrozen water to be drained away from the frozen DMSO. Impurities from the initial crude DMSO may leave in the water being drained away. After the freeze off operation the normal process of purifying DMSO such as the processes described in Example 1 and Example 3 are resumed to further purify the mother liquor that was not drained away during the freeze off operation.

Example 7

In certain embodiments, ultraviolet germicidal irradiation may be used to disinfect the DMSO such that the final DMSO product has either a substantially reduced quantity of microorganisms present or no microorganisms are present. The application of ultraviolet germicidal irradiation may be carried out on the drum or various stages of the DMSO purification process. In certain embodiments, the ultraviolet germicidal irradiation is applied to a liquid stream of purified DMSO.

The above-described embodiments have a number independently useful individual features that have particular utility when used in combination with one another including combinations of features from embodiments described separately. There are, of course, other alternate embodiments which are obvious from the foregoing descriptions of the invention, which are intended to be included within the scope of the invention, as defined by the following claims.

I claim:
1. A method of purifying dimethyl sulfoxide comprising:
 a. providing a first dimethyl sulfoxide composition having impurities;
 b. freezing a portion of the first dimethyl sulfoxide composition on a first surface to form a second dimethyl sulfoxide composition having higher dimethyl sulfoxide purity than the first dimethyl sulfoxide composition;
 c. separating the second dimethyl sulfoxide composition from the first dimethyl sulfoxide composition;
 d. mechanically breaking the second dimethyl sulfoxide composition at the first surface;
 e. removing the second dimethyl sulfoxide composition from the first surface thereby creating a clean portion of the first surface;
 f. continuously contacting the clean portion of the first surface with the first dimethyl sulfoxide composition; and
 g. melting a portion of the second dimethyl sulfoxide composition;
 h. wherein the freezing of the portion of the first dimethyl sulfoxide composition, the separating of the second dimethyl sulfoxide composition from the first dimethyl sulfoxide composition, and the melting of the portion of the second dimethyl sulfoxide composition happen simultaneously; and
 i. wherein the first surface is a rotating surface.

2. The method of purifying dimethyl sulfoxide of claim 1 wherein the freezing of the portion of the first dimethyl sulfoxide composition is carried out continuously for a period of time greater than 10 hours.

3. The method of purifying dimethyl sulfoxide of claim 1 wherein the freezing of the portion of the first dimethyl sulfoxide composition is carried out continuously for a period of time greater than 20 hours.

4. The method of purifying dimethyl sulfoxide of claim 1 wherein the freezing of the portion of the first dimethyl sulfoxide composition on the first surface has an efficient freezing duration greater than 50 minutes.

5. The method of purifying dimethyl sulfoxide of claim 1
 a. wherein the freezing of the portion of the first dimethyl sulfoxide composition on the first surface has an efficient freezing duration greater than 200 minutes;
 b. wherein the second dimethyl sulfoxide composition is mechanically separated from the second dimethyl sulfoxide composition; and
 c. wherein the melting of the portion of the second dimethyl sulfoxide composition takes place on a second surface.

6. The method of purifying dimethyl sulfoxide of claim 1 wherein the freezing of the portion of the first dimethyl sulfoxide composition on the first surface is done such that a maintained dimethyl sulfoxide ice thickness is less than 0.2 inches.

7. The method of purifying dimethyl sulfoxide of claim 1 wherein the freezing of the portion of the first dimethyl sulfoxide composition on the first surface is done such that a maintained dimethyl sulfoxide ice thickness is less than 0.4 inches.

8. The method of purifying dimethyl sulfoxide of claim 1 wherein the freezing of the portion of the first dimethyl sulfoxide composition on the first surface is done such that a single freeze percentage is greater than 25%.

9. The method of purifying dimethyl sulfoxide of claim 1 wherein a 4 hour productivity is greater than 15 $lb_m/ft^2$.

10. The method of purifying dimethyl sulfoxide of claim 1 wherein the freezing of the portion of the first dimethyl sulfoxide composition on the first surface to form the second dimethyl sulfoxide composition is done in a single continuous freezing operation.

11. The method of purifying dimethyl sulfoxide of claim 1 wherein a batch conversion percentage is greater than 50%.

12. The method of purifying dimethyl sulfoxide of claim 1
 a. wherein the freezing of the portion of the first dimethyl sulfoxide composition is carried out continuously for a period of time greater than 10 hours;
 b. wherein the freezing of the portion of the first dimethyl sulfoxide composition on the first surface has an efficient freezing duration greater than 50 minutes; and
 c. wherein the freezing of the portion of the first dimethyl sulfoxide composition on the first surface is done such that a maintained dimethyl sulfoxide ice thickness is less than 0.2 inches.

13. The method of purifying dimethyl sulfoxide of claim 12
 a. wherein the freezing of the portion of the first dimethyl sulfoxide composition on the first surface is done such that a single freeze percentage is greater than 25%;
 b. wherein a 4 hour productivity is greater than 15 $lb_m/ft^2$;
 c. wherein a single batch of dimethyl sulfoxide is frozen in a single continuous freezing operation; and
 d. wherein a batch conversion percentage is greater than 50%.

14. The method of purifying dimethyl sulfoxide of claim 1 wherein water is added to the first dimethyl sulfoxide composition prior to the step of freezing the portion of the first dimethyl sulfoxide composition.

15. The method of purifying dimethyl sulfoxide of claim 1 further comprising the step of applying ultraviolet germicidal irradiation to the second dimethyl sulfoxide composition.

16. The method of purifying dimethyl sulfoxide of claim 1 wherein the first surface is part of a rotating drum.

17. The method of purifying dimethyl sulfoxide of claim 1 wherein the first surface is part of an apparatus that is internally cooled.

18. The method of purifying dimethyl sulfoxide of claim 1 further comprising the step of mixing the first dimethyl sulfoxide composition.

\* \* \* \* \*